United States Patent [19]

John

[11] Patent Number: 5,607,409
[45] Date of Patent: Mar. 4, 1997

[54] STEAMING DEVICE FOR SKIN TREATMENT

[76] Inventor: Michael John, 8091 Hamptonwood Dr., Boca Raton, Fla. 33433

[21] Appl. No.: 543,810

[22] Filed: Oct. 16, 1995

[51] Int. Cl.$^6$ .............................. A61M 35/00; A61F 7/00
[52] U.S. Cl. .......................................... 604/289; 604/291
[58] Field of Search .................................. 604/289–291; 219/229, 56, 76.17, 71

[56] References Cited

U.S. PATENT DOCUMENTS

| | | | |
|---|---|---|---|
| 2,200,008 | 5/1940 | Nowak | 604/291 |
| 3,749,092 | 7/1973 | Williams | 604/291 |
| 4,292,971 | 10/1981 | Smit et al. | 604/291 |
| 5,098,414 | 4/1992 | Walker | 604/291 |

*Primary Examiner*—John G. Weiss
*Assistant Examiner*—David J. Cho
*Attorney, Agent, or Firm*—M. K. Silverman

[57] ABSTRACT

A steaming device for skin treatment includes a base, having an upper and lower surface, the base including a reservoir for water and a non-corrodible conductance element which is defined by two side-by-side vertically positioned electrodes which extend a part of the height of the reservoir. The electrodes diverge from each other as they approach the bottom of the bottom of the base to reduce current flow between them, this compensating for increased conductivity due to mineralization of the water near the bottom of the reservoir that occurs with vaporization and which mineralization would otherwise increase voltage between electrodes to a hazardous level. The device further includes a top portion including an upper and a lower area, and a container for therapeutic substances to be mingled with steam produced by the effect of the conductance element on the water. The device also includes an arm having a proximal and distal end, and hollow interior, in which the arm communicates with the top portion at the arm's proximal end and in which the arm includes an expulsory aperture enabling steam to escape at the distal end of the arm.

9 Claims, 3 Drawing Sheets

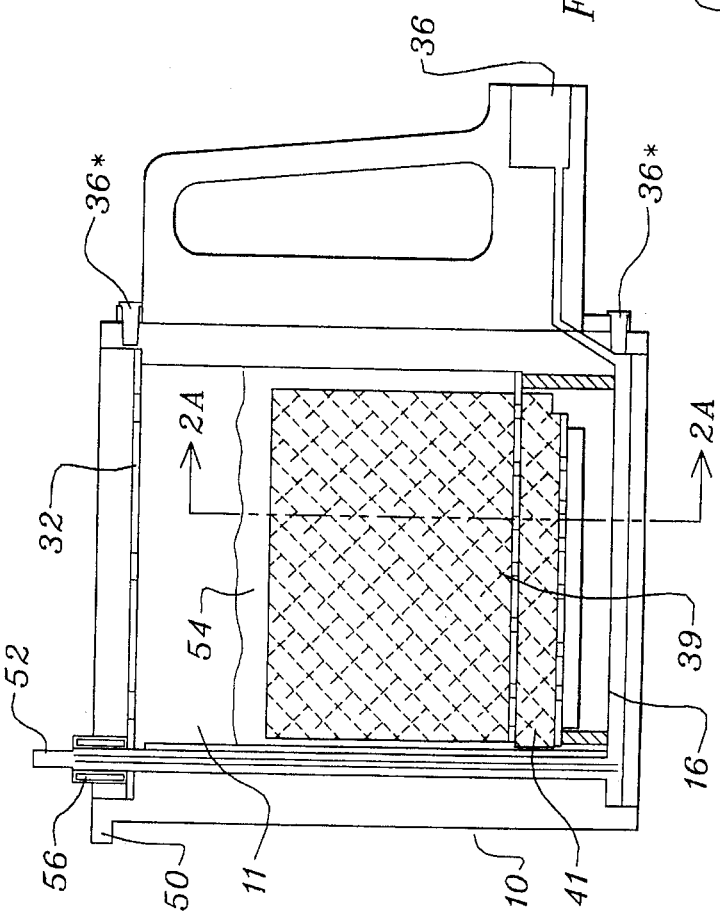
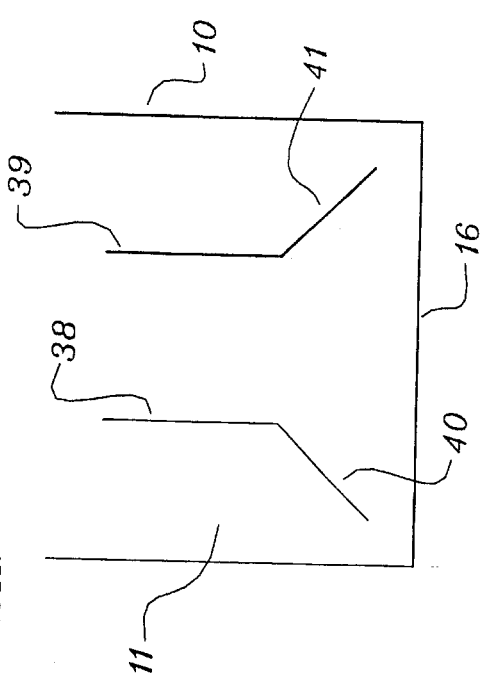
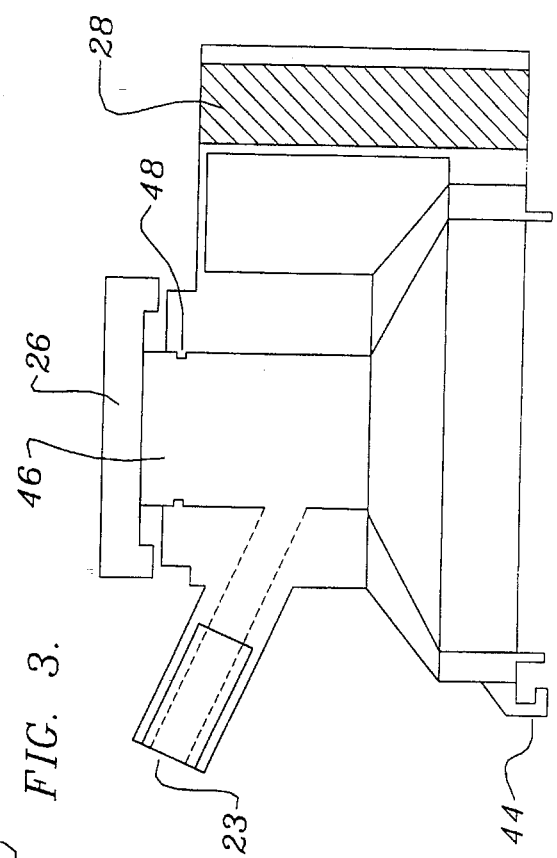
FIG. 2.
FIG. 2A.
FIG. 3.

STEAMING DEVICE FOR SKIN TREATMENT

REFERENCE TO RELATED APPLICATION

This application is a substitute of application Ser. No. 08/348,476, entitled Skin Care Vaporizer to Produce Steam for Skin Moisturization, filed Nov. 20, 1994.

BACKGROUND OF THE INVENTION

This invention relates to an article for boiling water and directing the steam to selected areas of the skin. This invention provides a significant improvement in that one can quickly and inexpensively superheat water to obtain steam, then co-mingle that steam with desired herbs or oils, and then readily direct the steam for skin care purposes, these advantages being without the risk of overheating of such steam or of the entire system, which existed in prior art systems, as set forth below.

The prior art, as is known to the inventor, entails the use of water placed in contact with heated elements, generally heated by electrical current, which produce steam which is then directed at the desired locale. These devices generally require a significant amount of time to for the elements to heat sufficiently to produce steam. Further, these devices typically produce many by-products through electrolysis which coagulates the by-products on the heating element, these products include calcium, fluoride, chlorine and certain minerals.

For example, U.S. Pat. No. 5,098,414 to Walker entitled Steaming Device for Cosmetic Skin Treatment, uses a reservoir to contain a predetermined quantity of water, a heater, a nozzle for directing the steam which nozzle can selectively vary the flow rate and direction thereof. However, Walker teaches the use a conventional heating element in a base plate, which is subject to the previously discussed corrosion problems. Walker also teaches the use of an induction motor to force air into and, thus, steam out of the device. In distinction, the instant invention relies upon the pressure of the steam to expel it from the nozzle. Also, Walker does not teach the co-mingling of steam with desired substances, at does the instant invention.

U.S. Pat. No. 4,616,122 to Burian and No. 4,399,349 to Deming, et al, both teach a stationary steamer, with unidirectional steam expulsion. Such devices also include conventional heat elements for steam generations, and, further, drive means expulsory movement of the steam. These devices also lack the directional control of the steam that the instant invention provides. Nor do these devices teach the co-mingling of steam with beneficial substances such as herbs and oils without leaving of by-products.

U.S. Pat. No. 4,190,052 to McCarthy, entitled Steam Facial Apparatus, teaches steam expulsion into an attached hose and convention heating of the water in a "boiler" apparatus, as well as the use of an air mover to interact with the steam. McCarthy does not teach a device which enables the steam to co-mingle with substances before expulsion, as does the instant invention.

U.S. Pat. No. 3,749,092 to Williams entitled Facial Treatment Apparatus, uses an omni-directional motor to direct air, which gives the device the ability to direct steam through a hose, and to use the same hose as a vacuum. Williams also teaches the use of two electrodes which causes a current to pass through the water, generating the steam. Williams does not allow the innate pressure and inertia of the steam to drive itself steam out of the apparatus, as does the instant invention. Further, the instant invention does not utilize a blower motor and cannot create a vacuum as does William's device. Williams device also does not allow for the co-mingling of the steam with other substances before expulsion.

None of these, or other references known to the inventor, address all of the problems solved by the present invention, that is, superheating in a safe fashion with non-corrodible elements, co-mingling steam with desired substances, and directing the steam to desired areas of skin to be treated.

SUMMARY OF THE INVENTION

The inventive steaming device for skin treatment includes a base, having an upper and lower surface, said base including a reservoir for water and a non-corrodible conductance element which is defined by two side-by-side vertically positioned electrodes which extend a part of the height of said reservoir. Said electrodes diverge from each other as they approach the bottom of said base to thereby reduce current flow therebetween, this compensating for increased conductivity due to mineralization of the water near the bottom of the reservoir that occurs with vaporization and which mineralization would otherwise increase voltage between the electrodes, such mineralization having caused hazardous overheating in the prior art. The device further includes a top portion including an upper and a lower area, and a fluid permeable container for therapeutic substances, such as herbs and to be mingled with steam produced by the effect of said conductance element on said water. The device also includes an arm having a proximal and distal end, and hollow interior, in which said arm communicates with said top portion at said arm's proximal end and in which said arm includes an expulsory aperture enabling steam to escape at said distal end of said arm.

It is an object of the invention to provide a device for the efficient and safe use of steam for purposes of skin treatment.

It is another object to provide a device which uses a non-corrodible means for heating water to produce steam, that is not subject to overheating.

It is yet a further object to provide a device which allows the co-mingling of steam and substances, such as herbs and oils, before expulsion of the steam from the device, for purposes of aromatherapy.

It is a yet further object of the invention to provide an economic device, built of durable materials, which can provide steam for skin treatment.

It is another object to provide a device which can superheat water to quickly provide steam of a constant temperature for skin treatment.

The above and yet other objects and advantages of the invention will become apparent from the hereinafter set forth Brief Description of the Drawings, Detailed Description of the Invention and Claims appended herewith.

BRIEF DESCRIPTION OF THE DRAWINGS

FIG. 2 is a side cross-sectional view of the bottom thereof.

FIG. 2A is a cross-sectional view taken along Line 2A—2A of FIG. 2.

FIG. 3 is a cross sectional of the top portion of the steaming device.

DETAILED DESCRIPTION OF THE INVENTION

Figure 1:
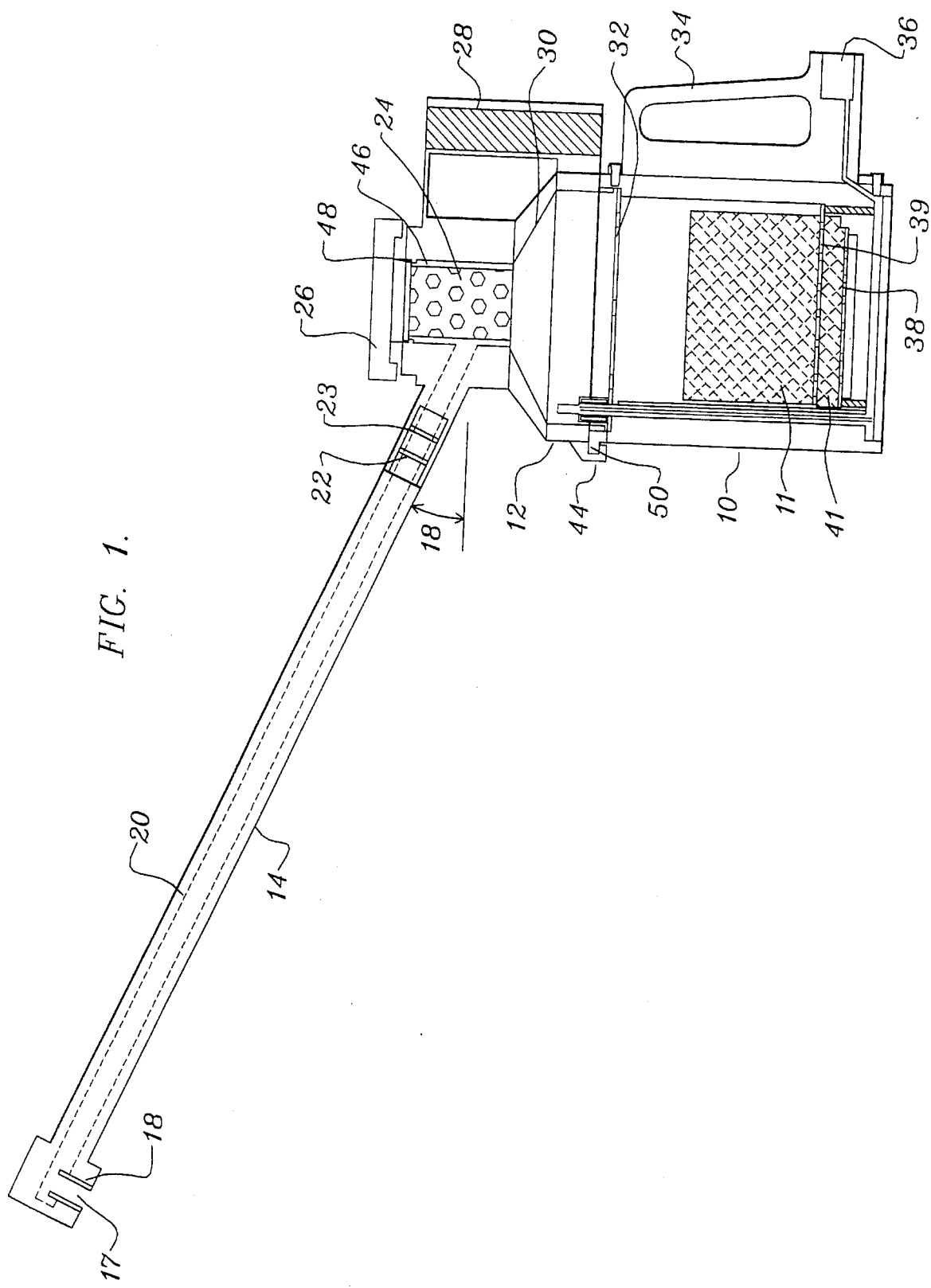
FIG. 1 is an side cross-sectional view of the steaming device.

As shown in FIGS. 1 and 2, the instant steaming device includes a base 10, a top portion 12, and an arm 14. The base 10 includes a dependent handle 34, and also contains a water reservoir 11 with two vertical conductance elements or electrodes 38 and 39 which diverge from each other at the lower area of the reservoir 11 (see FIG. 2A). The electrodes are connected to an external source of electricity 36 and intermittently pass an electrical current therebetween and through the water in the reservoir 11, thus superheating the water to create steam upon the release of the superheated water into arm 14.

The electrodes 38 and 39 are preferably positioned vertically, i.e., at right angles to a lower surface 16 of base 10. As may be noted with reference to the cross-sectional view of FIG. 2A, parts 40 and 41 of said electrodes 38 and 39 respectively diverge from each other as they approach said surface 16 to thereby reduce current flow therebetween. This divergence compensates for increased conductivity due to mineralization of water near the bottom of the reservoir that occurs with vaporization. Such mineralization would otherwise increase voltage between electrodes to cause a hazardous over-heating of the device and/or the superheated steam. Such over-heating has posed a major problem in the prior art. However, with such divergence of the electrodes a substantially constant voltage and, therefore, temperature can be maintained.

With further reference to FIG. 2, it may be seen that the base 10 includes a switch 52 at its upper end, which uses a float 56 to monitor a level 54 of water in the reservoir 11. If the water level 54 is too high, it presses against the float 56 which causes the switch 52 to cut the electricity off, precluding any electrical hazard. Further, upper area of base 10 includes a perforated security plate 32, covering the water reservoir 11, which prevents boiling water from splashing or spitting out, while allowing the steam to escape therethrough to the arm 14.

With reference to FIGS. 1 and 2, the base 10 also has, at its upper outward edge, a lip 50 upon which a superior lip 44 at a lower end of top portion 12 fits over to thereby lock the top portion onto the base 10.

Figure 4:
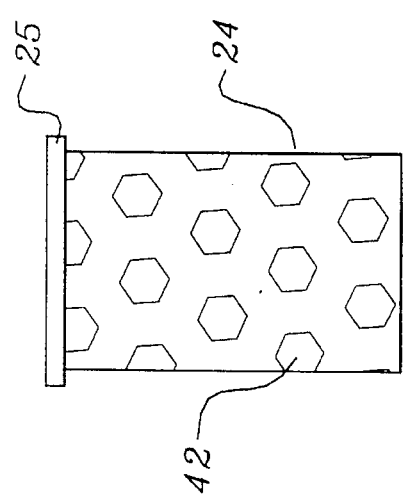
FIG. 4 is an side view of the container for therapeutic substances to be mingled with steam from the device.

Top portion 12 (see FIGS. 1 to 4) also includes a handle 28, a perforated or fluid permeable container 24 for therapeutic substances to be mingled with the steam, before entering arm 14, and a receiving region 46 for the container 24. A lid 26 covers the region 46 while and an outward tube 23 slides into which the arm 14. The container 24 has small perforations 42 which allow the steam to pass through the contents of the container, which may include herbs used in aromatherapy before exiting to the arm 14. The container 24 also has an outward lip 25 (see FIG. 4) at its circumferential upper end, which rests upon an inner lip of in the interior of the container compartment 46. Once the lid 26 is placed on the top portion 12, the perforated container 24 is firmly locked within the container compartment 46, forcing the steam out and into the arm 14.

Alternately, the perforated container 24 which allows steam to pass through its contents before exiting to the arm, may be integral with the perforated security plate 32, and thereby accessible once the top 12 is removed.

Figure 5:
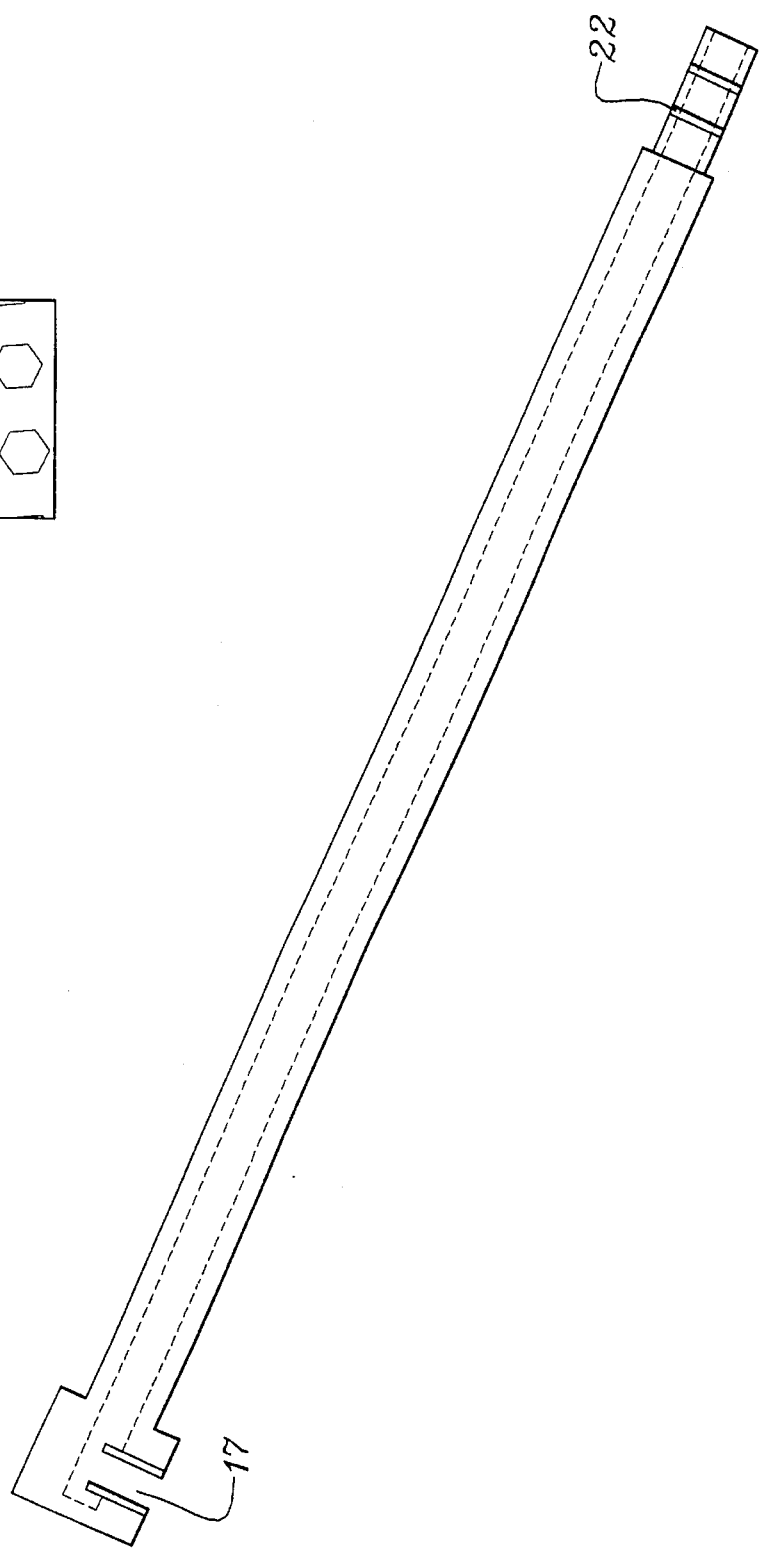
FIG. 5 is an axial cross sectional view of the arm of the device.

The arm 14 (see FIGS. 1 and 5) includes a ridged end 22 which fits into the top 12, a hollow tubular center 20, and aperture 17 through which the steam passes from the base 10. An angle 18 between the arm 14 and the horizontal is between 0 and 60 degrees, with 30 degrees being optimal.

It is noted that the present inventive steaming device may be formed in whole or in part of heat-and-shock resistant plastic and/or metal.

Accordingly, while there has been shown and described the preferred embodiment of the device, it is to be understood that the invention may be embodied otherwise than is herein specifically shown and described and that within said embodiments, certain changes may be made in the forms and arrangements of the parts without departing from the underlying ideas or principles of this invention as set forth in the Claims appended herewith.

Having thus described my invention, what I claim as new, useful, and non-obvious and, accordingly, secure by Letters Patent of the United States is:

1. A steaming device for skin treatment, comprising:
   (a) a base, including an upper and lower surface thereof, said base including a reservoir for water and a non-corrodible conductance means, said means comprising two electrodes substantially vertically positioned, each extending a part of the entire height of said reservoir in said base, in which said electrodes intermittently pass an electrical current through water within said reservoir;
   (b) a top portion including an upper and a lower area, and a fluid permeable container for therapeutic substances to be mingled with steam produced by the effect of said electrodes on said water; and
   (c) an arm having a proximal and a distal end, and a hollow interior, in which said arm communicates with said top portion at said proximal end of said arm and in which said arm includes an expulsory aperture enabling the steam which has been mingled with said therapeutic substances to escape at said distal end of said arm.

2. The device as recited in claim 1, in which said electrodes diverge from each other near the bottom of said height of said reservoir.

3. The steaming device as recited in claim 1, in which said top container comprises means for the containment of said substances to enable them to interact with said steam.

4. The steaming device as recited in claim 2, in which said container including means for the containment of said substances to enable them to interact with said steam.

5. The steaming device as recited in claim 3, in which said top portion includes means for snap-fittable engagement onto said upper surface of said base.

6. The steaming device as recited in claim 3, in which said base includes a perforated security plate at said upper area of said base.

7. The steaming device as recited in claim 3, in which said arm includes means for elevation between 0 and 60 degrees from horizontal.

8. The steaming device as recited in claim 3, in which said device is comprises heat-and-shock resistant plastic.

9. The steaming device as recited in claim 1, in which said device comprises a metal.

* * * * *